United States Patent [19]
Nishioka et al.

[11] Patent Number: 4,584,988
[45] Date of Patent: Apr. 29, 1986

[54] ILLUMINATION APPARATUS FOR ENDOSCOPE

[75] Inventors: Kimihiko Nishioka, Tokyo; Hiroyuki Kimura, Oosaka, both of Japan

[73] Assignee: Olympus Optical Co., Ltd., Tokyo, Japan

[21] Appl. No.: 645,158

[22] Filed: Aug. 28, 1984

[30] Foreign Application Priority Data

Sep. 2, 1983 [JP] Japan .................. 58-161483
Sep. 19, 1983 [JP] Japan .................. 58-172379

[51] Int. Cl.⁴ .............................................. A61B 1/06
[52] U.S. Cl. ................................................. 128/6
[58] Field of Search ................................. 128/4, 6

[56] References Cited

U.S. PATENT DOCUMENTS 4,253,447 3/1981 Moore et al. ................ 128/6

FOREIGN PATENT DOCUMENTS 47-41639 12/1972 Japan .
5310200 1/1975 Japan .
54-89749 7/1979 Japan .
55-12204 3/1980 Japan .
56-125203 11/1981 Japan .

Primary Examiner—William H. Grieb

[57] ABSTRACT

An illumination apparatus for an endoscope is provided at the distal end of the insertion section of the endoscope. The apparatus has a light guide which extends through the insertion section, has a light-issuing end located adjacent to the distal end opening of the insertion section. The light guide conducts light beams emitted from a light source device. An optical element made of a light-permeable material is arranged to face the light-issuing end of the light guide, and a lens is arranged in the distal end opening. The optical element has a light-receiving surface facing the light issuing end and a light issuing surface opposite to the lens. A depression is formed in the center of the light-issuing surface. Light beams emitted from the end of the light guide pass through the optical element and lens, and are distributed by the depression in the annular pattern whose central portions grow dark and whose peripheral portions are rendered bright.

14 Claims, 19 Drawing Figures

ILLUMINATION APPARATUS FOR ENDOSCOPE

BACKGROUND OF THE INVENTION

This invention relates to an endoscope whose illumination optical system has been improved.

In recent years, the number of foreground subjects to be observed by an endoscope has grown in the fields of medical treatment and manufacturing industries, and has assumed extremely diversified forms. Sometimes a wide angle is preferred, depending on the type of foreground subject to be examined. As a result, the range of the illumination carried out by the endoscope illumination apparatus has to be widened. To meet this requirement, various attempts, including the use of a wide angle lens, have been made. However, none of the proposals advanced to date have been able to realize a sufficiently wide illumination angle. Moreover, the illumination by the conventional illumination apparatus is brightest at its center and grows progressively darker toward its periphery. When, therefore, observation was made of the inner walls of, for example, the alimentary canal or intestines which are located at the peripheral portions of the illumination range of the apparatus, it was difficult to distinctly observe the subject due to the great darkness prevailing over the peripheral portions. In such a case, the light at the center of the illumination range of the illumination apparatus made no contribution to the observation of the above-mentioned inner walls and was simply wasted. Therefore, the conventional illumination apparatus is accompanied with the drawback that its illumination efficiency was considerably unsatisfactory.

SUMMARY OF THE INVENTION

This invention has been accomplished in view of the above-mentioned circumstances and is intended to provide an illumination apparatus for an endoscope which enables its illumination range to be widened and also the peripheral portions of the illumination range to be supplied with a sufficient amount of light, thereby ensuring the efficient illumination of the inner wall of a tubular foreground subject.

To attain the above-mentioned object, this invention provides an illumination apparatus for an endoscope which comprises:

an optical element whose light-receiving surface faces the light-issuing end of a light guide of an endoscope;

a lens arranged opposite to a light-issuing surface of the optical element, and wherein a depression is formed at the center of the light-issuing surface of the optical element.

An illumination apparatus according to one aspect of this invention which is arranged as described above offers the advantages that the range of illumination is widened; light beams emitted from the optical element and conducted through the lens can be so distributed that the central part of the illumination range grows darker, whereas the peripheral portions of the illumination range conversely become brighter.

An illumination apparatus according to another aspect of the invention is characterized in that the light-issuing surface of the optical element is separated by a distance g determined by the following equation from a point conjugate with that plane which is assumed to face a foreground subject. The illumination range can be widened, thereby enabling a uniform amount of light to be distributed through the illumination range.

$$|g| \geq D/2 \tan \alpha$$

$\alpha$: Emission angle (degrees) of a light beam
$D$: Diameter (mm) of the depression measured in the plane of the light-issuing surface.

DETAILED DESCRIPTION OF THE PREFERRED EMBODIMENTS

Figure 1:
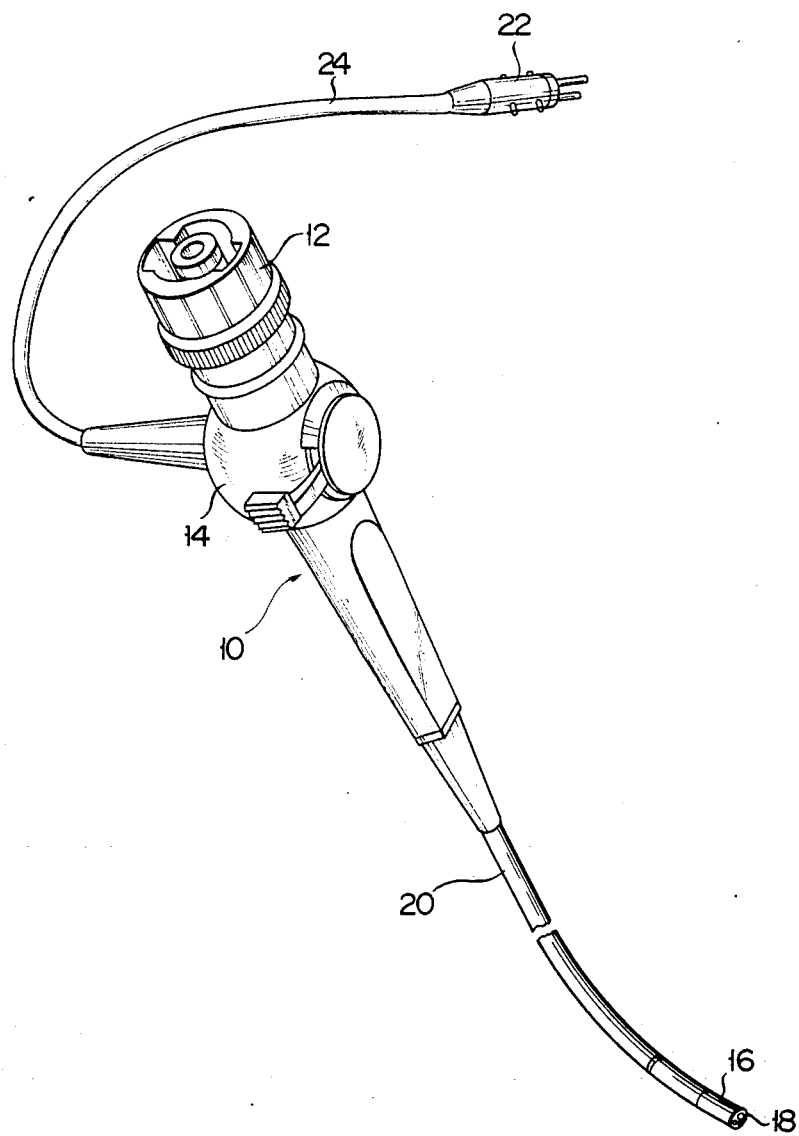
FIG. 1 is a perspective view of the whole endoscope.

A description may now be made of the preferred embodiments of this invention with reference to the accompanying drawings. FIG. 1 shows the whole endoscope. The endoscope 10 comprises an operation section 14 fitted with an eyepiece 12, an insertion section 20 which extends from the operation section and has an illumination window 18 formed at the distal end 16, and a flexible tube 24 which extends from the operation section 14 and is connected to a light source device (not shown) through a connector 22. A light guide 26 (FIG. 2) extends from the connector 22 to the proximity of the illumination window 18 through the flexible tube 24, operation section 14 and insertion section 20. When the connector 22 is connected to the light source device, light beams emitted from the light source device are conducted throgh the light guide 26 to the distal end 16 of the insertion section 20.

Figure 2:
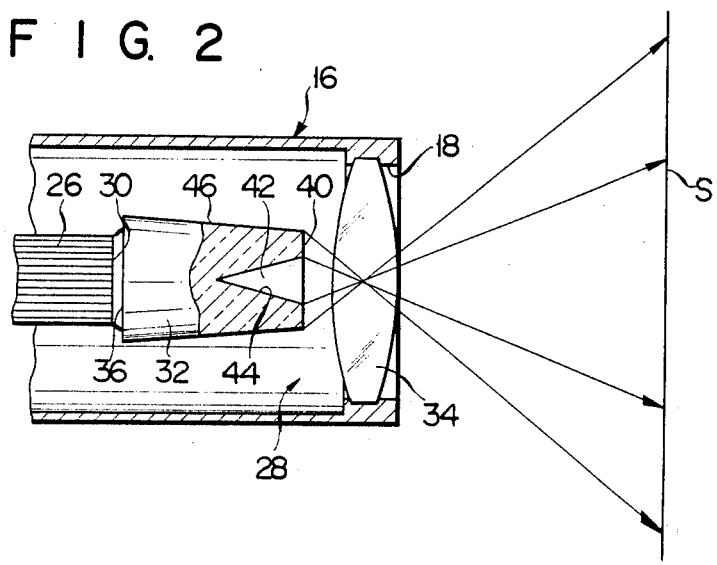
FIG. 2 is a side view of an optical system involved in an illumination apparatus according to one embodiment of this invention.

As shown in FIG. 2, the distal end 16 of the insertion section 20 is fitted with an illumination apparatus 28 embodying this invention. This illumination apparatus 28 comprises an optical element 32 optically connected to the light-issuing end 30 of the light guide 26 and a convex lens 34 fitted to the illumination window 18 so as to face the optical element 32. The optical element 32 is made from a light-permeable material and has a circular truncated conical shape. The end face on the larger diameter side of the optical element 32 acts as a light-receiving surface 36. The optical element 32 is concentrically arranged with the light guide 26. The light-receiving surface 36 faces the light-emitting end 30 of the light guide 26, thereby effecting an optical connection between both elements 32, 36. The end face of the smaller diameter side of the optical element 32 acts as a light-issuing end face 40 and faces the convex lens 34. A conical depression 42 is coaxially formed in the light-issuing end face 40, thereby causing the light-issuing end face to assume an annular form. The shape of the depression 42 is so designed that when the light beams emitted from the light-issuing end face 40 pass through the convex lens 34, the distribution of light beams over the plane S, on which a foreground subject is assumed to be set, indicates the pattern shown in FIG. 3, in which the central portion of the illumination range grows darker, whereas the peripheral portion of the illumination range becomes brighter in the ring form. In other words, the light beams entering the optical element 32 from the light guide 26 are repeatedly reflected on the conical surface 44 of the depression 42 and on the outer peripheral surface 46 of the optical element 32, and are emitted from the light-issuing surface 40 in a ring form. When passing through the convex lens 34, the emitted light beams are converged and distributed in the pattern shown in FIG. 3.

When the inner wall 48 of a canal lying in the celiac cavity of, for example, a human body taken as a foreground subject, is illuminated by the illumination apparatus constructed as described above, light beams are concentrated on the inner wall of said celiac canal taken as the field of view X, thereby preventing the light beams from being uselessly emitted straight through the celiac canal.

Figure 5:
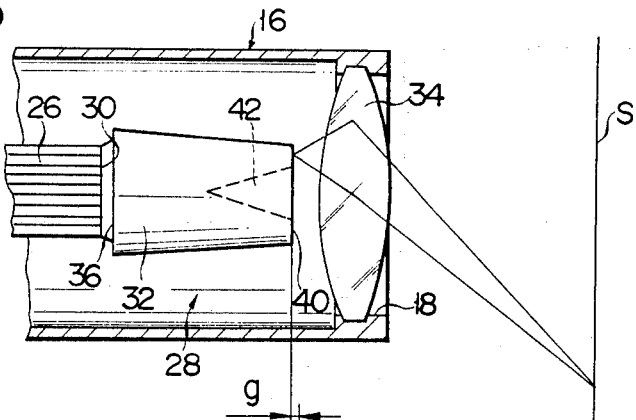
FIG. 5 shows the course taken by a light beams emitted from one point on the subject illumination apparatus.

As shown in FIG. 5, the light-issuing surface 40 of the optical element 32 assumes a conjugate position with respect to the plane S on which the foreground subject is assumed to be set, causing light beams emitted from one point on the light-issuing surface to be converged on the plane S after passing through the convex lens 34.

Figure 6:
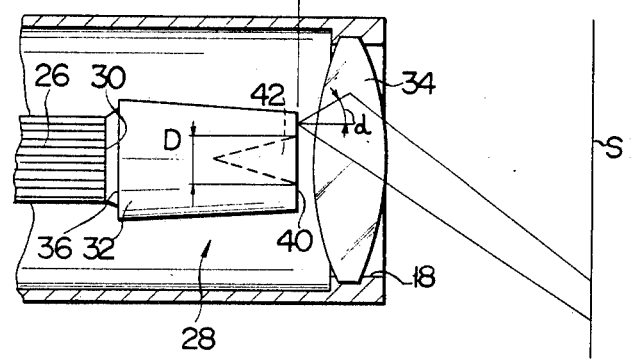
FIG. 6 is a side view of an illumination apparatus according to a first modification of the invention.

With the modification of FIG. 6, the optical element 32 is so positioned as to cause the light-issuing surface 40 to be displaced from the conjugate point shown in FIG. 5 toward the convex lens 34 at a distance g. As used herein, the distance g is defined by the following formula:

$$|g| \geq D/2 \tan \alpha$$

α: Emission angle (degrees) of a light beam
D: Diameter (mm) of the depression 42 measured in the plane of the light-issuing surface.

With the above-mentioned modification, light beams emitted from the light-issuing surface 40 of the optical element 32 in the ring form are focused due to a passage through the convex lens 34 having a positive focal point. Since, however, the light-issuing surface 40 of the optical element 32 is displaced from the conjugate point at the distance g, the light beams are not completely focused on the plane S on which a foreground subject is supposed to be set, but are irradiated on the plane S in the defocused form. Like the aforementioned embodiment, therefore, the modification of FIG. 6 offers the advantages that the illumination range can be broadened, and that light beams are irradiated on the plane S in a blurred form, thereby minimizing the irregular emission of light beams within the specified illumination range.

Figure 7:
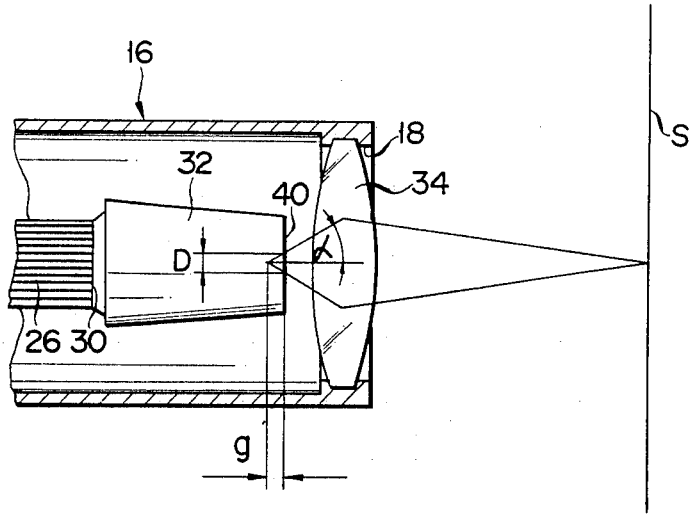
FIG. 7 illustrates the arrangement of said first modification showing its operation.

When, an shown in FIG. 7, the diameter D of the base of the conical depression 42 is larger than 2 g·tan α, light beams are not gathered in the same places on the plane S, giving rise to an irregular illumination.

Figure 8:
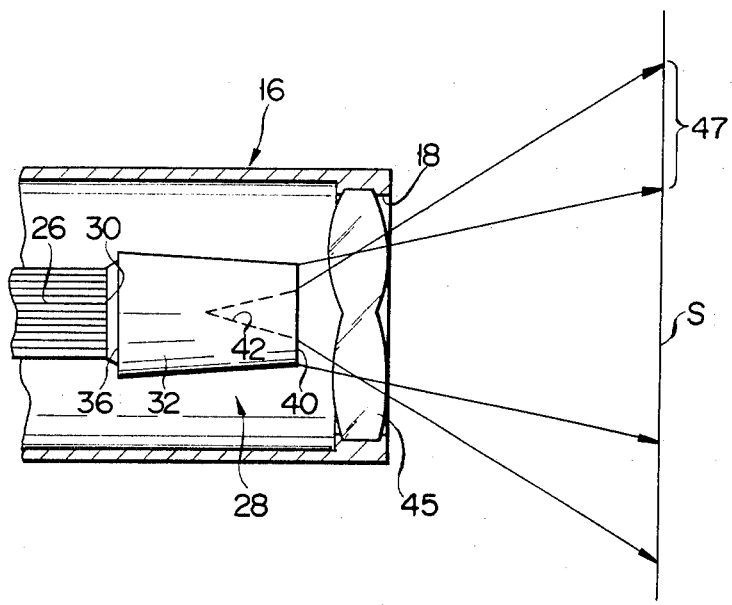
FIG. 8 is a partly cut-out side view of an illumination apparatus according to a second embodiment of the invention.

FIG. 8 shows a second embodiment of the invention. This second embodiment is substantially the same as the first embodiment, except that the convex lens 34 of the first embodiment is replaced by a double convex lens 45. This double convex lens 45 has such a cross-sectional outline as is obtained when the convex lens 34 of the first embodiment is rotated around the axis of the optical element 32. The double convex lens 44 has such an action that light beams emitted from the neighborhood of the inner peripheral portion of the light-issuing surface 40 of the optical element 32 illuminate the outer peripheral portion of the ring-shaped illumination range 47, and that light beams issued from the neighborhood of the outer peripheral portion of the light-issuing surface 40 are cast on the inner peripheral portion of the illumination range 47.

Figure 3:
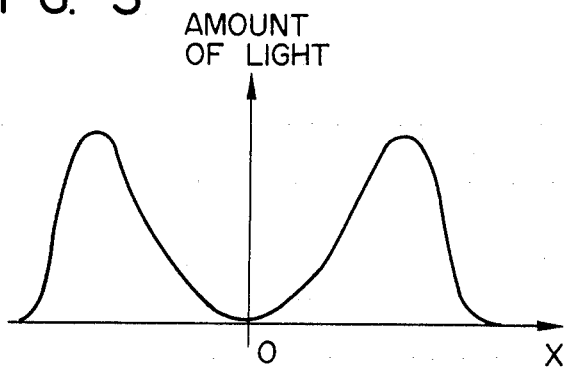
FIG. 3 shows the distribution of light emitted from the subject illumination apparatus.
Figure 4:
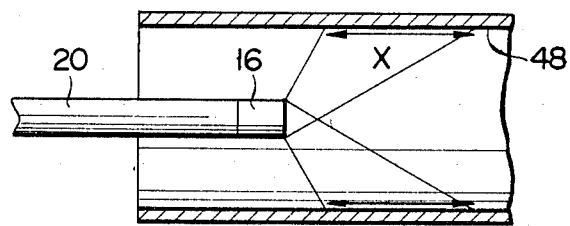
FIG. 4 illustrates the manner in which the illumination apparatus sheds light beams over the inner wall of one of the canals lying in the celiac cavity of, for example, a human body taken as a foreground subject.
Figure 9:
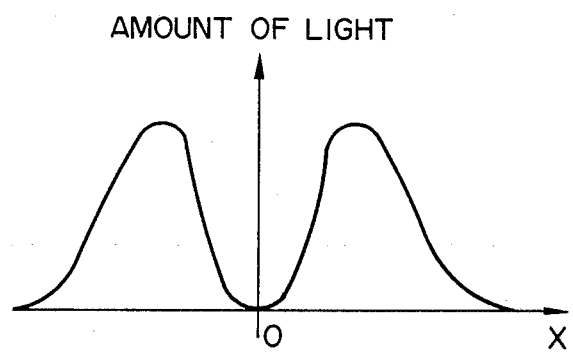
FIG. 9 indicates the distribution of light beams issued from the illumination apparatus according to the second embodiment.

With the second embodiment of FIG. 8, therefore, the distribution of light beams has the pattern as shown in FIG. 9. Namely, the illumination peaks lie nearer to the inner peripheral portion of the ring-shaped illumination range 47 than in FIG. 3 representing the first embodiment. The amount of light progressively reduces as it moves toward the outside of the illumination range 47. When, the inner walls of the celiac canal are illuminated by the illumination apparatus, according to the second embodiment as shown in FIG. 4, a maximum amount of light beams is emitted to the remotest portions of the inner walls, and a smaller amount of light beams is irradiated on those portions of the inner walls which lie nearer to the light-issuing surface 40 of the optical element 32. As a result, a uniform illumination can be realized throughout the inner walls of the celiac canal.

Figure 10:
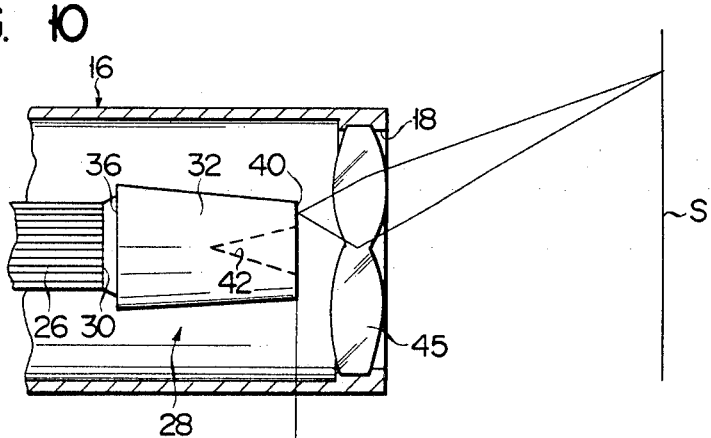
FIG. 10 shows the course taken by the light beams emitted from one point on the illumination apparatus of FIG. 8.
Figure 11:
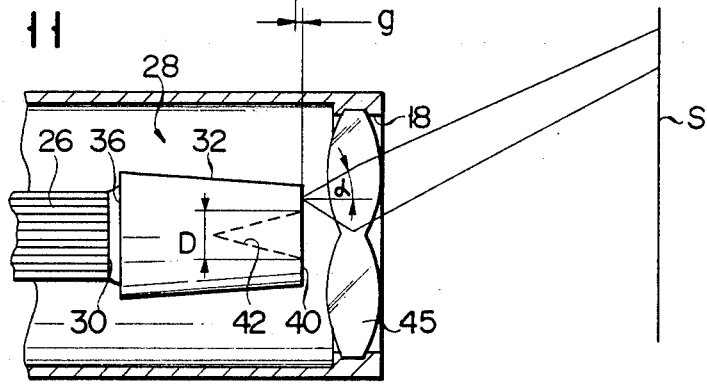
FIG. 11 sets forth the arrangement of an illumination apparatus according to the second modification of the invention.

When, as seen from FIGS. 10 and 11, the light-issuing surface 40 of the optical element 32 is displaced from the conjugate point toward the lens 45 at the distance g, the illumination range can be broadened, and any irregularities of illumination within the specified range can be reduced.

Figure 12:
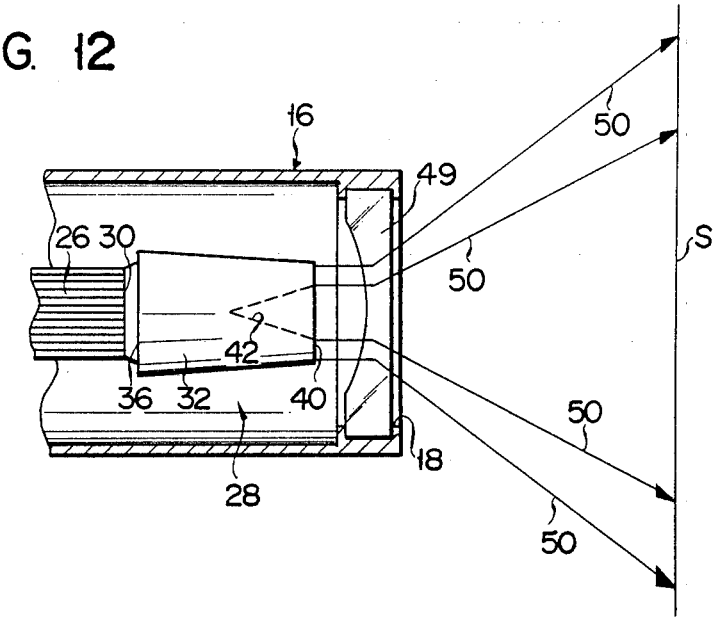
FIG. 12 is a partly cut-out side view of an illumination apparatus according to a third embodiment of the invention.

FIG. 12 shows a third embodiment of the invention. This third embodiment is substantially the same as the first embodiment except that the convex lens 34 of the first embodiment is replaced with a concave lens 49.

Figure 13:
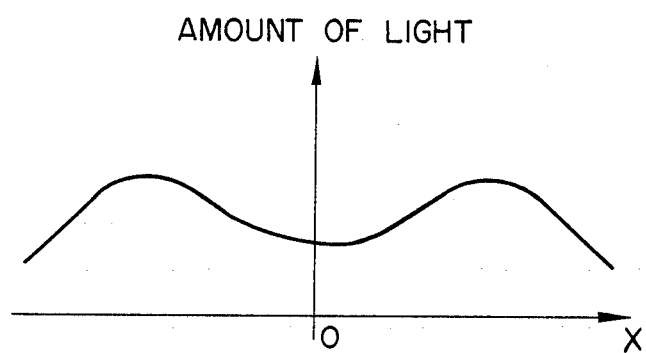
FIG. 13 indicates the distribution of light beams emitted from the illumination apparatus according to the third embodiment.

With this third embodiment, the light beams 50 having the greatest intensity among those emitted from the light-issuing surface 40 of the optical element 32 are initially conducted in parallel with the optical axis of the element 32. However, the light beams 50 are diverted outward toward the periphery by the action of the concave lens 49. Therefore, a ring-shaped illumination is realized with the intensity of the light beams gently distributed as shown in FIG. 13.

Figure 14:
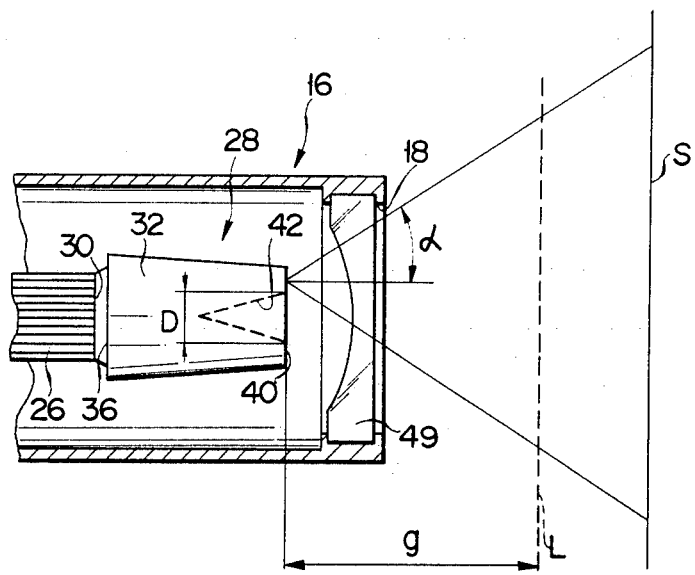
FIG. 14 set forth the arrangement of an illumination apparatus according to a third modification of the invention.

With the modification of FIG. 14, the optical element 32 and concave lens 49 assume such a position that the distance g between the point L at which the foreground subject plane S produces a virtual image, and the light-issuing surface 40 of the optical element 32 assumes a value determined by the following equation:

$$g \geq D/2 \tan \alpha$$

α: Emission angle of light beams
D: Diameter of the depression measured in the plane of the light-issuing surface.

Like the aforementioned modification, the modification of FIG. 14 offers the advantage that the illumination range can be broadened, and illumination irregularities can be reduced.

Figure 15:
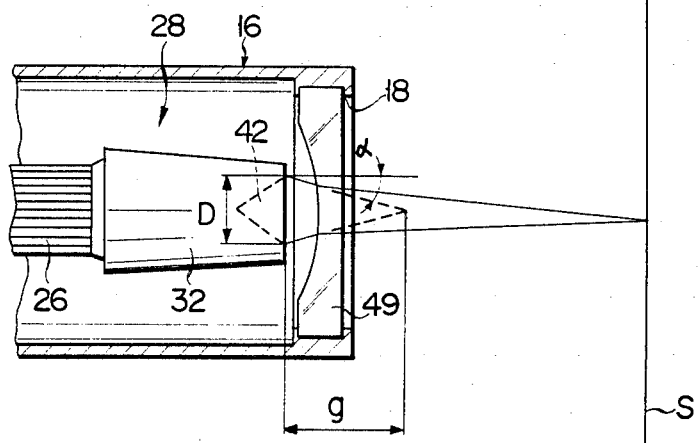
FIG. 15 illustrates the operation of the third modification.

When the diameter D of the base of the conical depression 42 is larger than 2g tan α as shown in FIG. 15, light beams are not gathered in some places on the plane S on which the foreground subject is assumed to be set, thereby giving rise to illumination irregularities.

Figure 16:
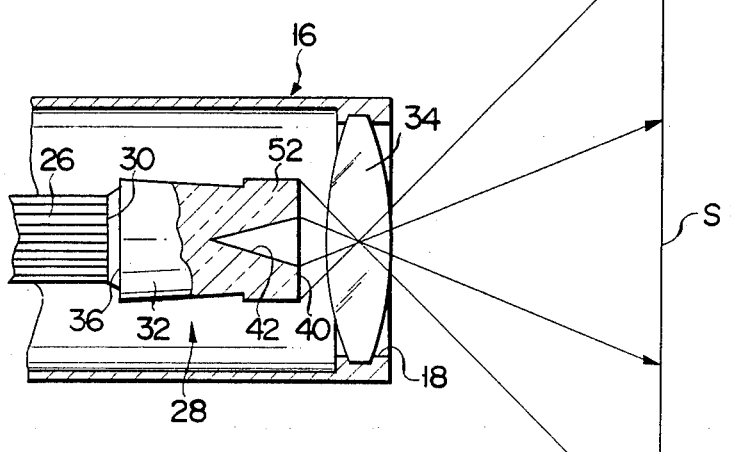
FIG. 16 is a partly cut-out side view of an illumination apparatus according to a fourth modification.
Figure 17:
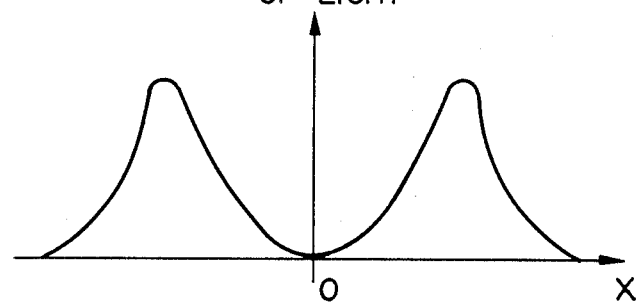
FIG. 17 shows the distribution of light beams emitted from the fourth modification.

A description may now be made with reference to FIG. 16 of an illumination apparatus according to a fourth modification. With this fourth modification, an annular projection 52 is integrally formed on the outer periphery of the light-issuing surface 40 of the optical element 32 in order to increase the diameter of the outer peripheral portion of the light-issuing surface 40. The provision of the annular projection 52 has the effect that the quantity per unit area of the light beams emitted from the neighborhood of the outer periphery of the light-issuing surface 40 is reduced more than the quantity per unit area of the light beams issued from the neighborhood of the inner peripheral of the light-issuing surface 40. Therefore, the illumination on the outer peripheral portion of the annular illumination range is decreased more on the inner peripheral portion thereof, therby giving rise to the light beam distribution illustrated in FIG. 17.

Figure 18:
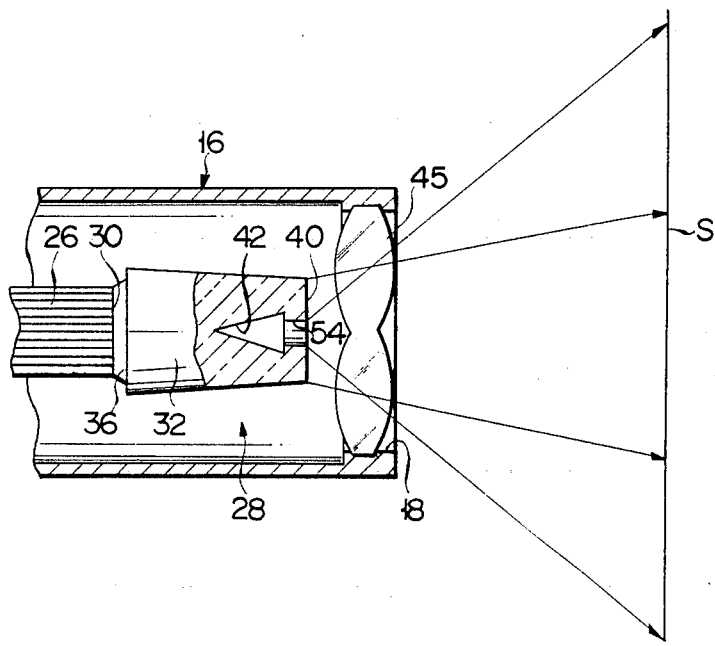
FIG. 18 is a partly cut-out side view of an illumination apparatus according to a fifth modification.
Figure 19:
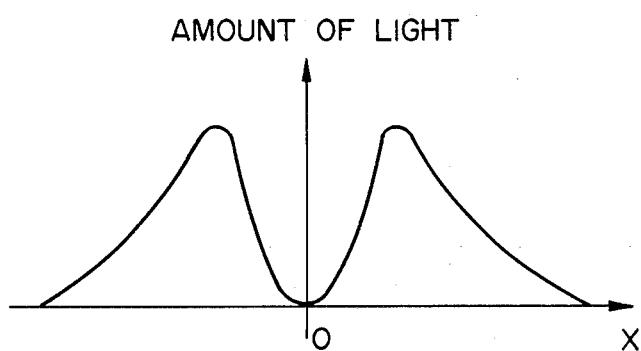
FIG. 19 shows the distribution of light beams issued from the fifth modification.

FIG. 18 shows a fifth modification of the invention. With this modification, an annular projection 54 is integrally formed on the inner peripheral wall of the conical depression 42 of the optical element 32 in order to broaden the inner peripheral edge portion of the light-issuing surface 40 of the optical element 32. The provision of the annular projection 54 has the effect that the guantity per unit area of the light beams issued from the neighborhood of the inner peripheral portions of the light-issuing surface 40 is reduced more than the quantity per unit area of the light beams sent forth from the neighborhood of the outer peripheral portions of the light-issuing surface 40. As compared with the second embodiment, therefore, the fifth modification of FIG. 18 is characterized in that the illumination is more uniformly reduced from the inside toward the outside of the annular illumination range as illustrated in FIG. 19.

It will be noted that this invention is not limited to the foregoing embodiments and modifications, but that it is also practical with further changes and modifications.

For instance, the light-receiving surface and light-issuing surface of the optical element need not be flat, but may assume any other form, for example, a concave, convex, or nonspherical form. Further, the optical element need not assume a circular truncated conical shape, but may be formed in the shape of a rounded column, key, or hourglass. The depression need not assume a conical form, but may be formed in a spherical or angular conical shape. The inner peripheral wall of the depression need not be linear, but may be concave, convex or curved.

The outer peripheral wall of the optical element and the inner wall of the depression need not be prepared from a transparent material, but may be formed of a translucent or light-reflecting material.

The optical element may be provided by grinding glass material or may be formed of synthetic resin. Synthetic resin molding particularly facilitate the manufacture of the optical element. The optical element has only to be optically connected to the light-issuing surface of a light guide, and need not be physically pressed against the light-issuing plane.

What is claimed is:

1. An illumination apparatus for an endoscope provided with a narrow insertion section open at the distal end and connected to a light source device, comprising:

a light guide, which extends through the insertion section, said guide being provided with a light-issuing end disposed adjacent to the distal end opening of the insertion section, and which conducts light beams emitted from the light source device;

an optical element, which is prepared from a light-permeable material, facing the light-issuing end of the light guide, said optical element being provided with a light-receiving surface which is exposed to light beams emitted from the light-issuing surface facing the light-receiving surface and which transmits light beams delivered from the light-receiving surface, and a peripheral surface between the light-receiving and issuing surfaces; and a lens arranged in the distal end opening to face the light-issuing surface of the optical element, and which allows for the permeation of light beams emitted from the light-issuing surface of the optical element and transmits the light beams from the distal end opening;

said optical element being provided with a depression formed in substantially the center of the light-issuing surface thereof, whereby the light beams from the light guide are repeatedly reflected on the peripheral surface of the optical element and on the inner surface of the depression, emitted from the issuing surface and conducted through the lens in an annular pattern whose central portions grow dark and whose peripheral portions are rendered bright.

2. The apparatus according to claim 1, wherein said optical element has a circular truncated conical shape, and the light-issuing surface is constituted by the smaller diameter end face of the optical element.

3. The apparatus according to claim 2, wherein said depression is formed in a conical shape.

4. The apparatus according to claim 3, wherein said depression is formed concentrically with the light-issuing surface of the optical element.

5. The apparatus according to claim 4, wherein said optical element has an annular projection protruding from the outer peripheral surface of the smaller diameter end portion of the optical element to broaden the light-issuing surface thereof.

6. The apparatus according to claim 4, wherein said optical element has an annular projection protruding from the inner peripheral wall of the depression to reduce the inner diameter of the light-issuing surface.

7. The apparatus according to claim 1, wherein said lens is a convex form, and its optical axis coincides with that of the optical element.

8. The apparatus according to claim 1, wherein said lens is a concave form, and its optical axis coincides with that of the optical element.

9. The apparatus according to claim 1, wherein said light-issuing surface of the optical element is displaced from a conjugate point at a distance g determined by the following formula with respect to that plane on which a foreground subject is assumed to be set:

$$|g| \geq D/2 \tan \alpha$$

where:

$\alpha$ = the emission angle of light beams issued from the light-issuing surface of the optical element $D$ = diameter of the depression measured in the plane of the light-issuing surface.

10. The apparatus according to claim 9, wherein said light-issuing surface of the optical element is displaced from the conjugate point toward the lens at the distance g.

11. The apparatus according to claim 9, wherein said optical element has a circular truncated conical shape, and the light-issuing surface is constituted by the smaller diameter end face of the optical element.

12. The apparatus according to claim 11, wherein said depression has a conical shape, and is formed concentrically with the light-issuing surface of the optical element.

13. The apparatus according to claim 9, wherein said lens is a convex type, whose optical axis is concentric with that of the optical element.

14. The apparatus according to claim 9, wherein said lens is a concave type, whose optical axis is concentric with that of the optical element.

* * * * *